(12) United States Patent
Le Couedic et al.

(10) Patent No.: US 9,295,496 B2
(45) Date of Patent: Mar. 29, 2016

(54) VERTEBRAL FIXATION DEVICE

(75) Inventors: Regis Le Couedic, Bordeaux (FR);
Christian Baccelli, Saucats (FR)

(73) Assignee: Implanet Societe Anonyme, Martillac (FR)

( * ) Notice: Subject to any disclaimer, the term of this patent is extended or adjusted under 35 U.S.C. 154(b) by 0 days.

(21) Appl. No.: 14/128,214

(22) PCT Filed: Jun. 27, 2012

(86) PCT No.: PCT/FR2012/000259
§ 371 (c)(1),
(2), (4) Date: Dec. 20, 2013

(87) PCT Pub. No.: WO2013/001180
PCT Pub. Date: Jan. 3, 2013

(65) Prior Publication Data
US 2014/0114356 A1    Apr. 24, 2014

(30) Foreign Application Priority Data

Jun. 30, 2011    (FR) ..................... 11 02072

(51) Int. Cl.
*A61B 17/70*    (2006.01)
*A61B 17/84*    (2006.01)

(52) U.S. Cl.
CPC ........... *A61B 17/7053* (2013.01); *A61B 17/707* (2013.01); *A61B 17/842* (2013.01); *A61B 17/7041* (2013.01)

(58) Field of Classification Search
CPC ........... A61B 17/7053; A61B 17/7022; A61B 17/82; A61B 17/823; A61B 17/826; A61B 17/842; A61B 17/0487; A61B 17/0401; A61B 2017/0414; A61B 2017/045; A61B 2017/0454; A61B 2017/0488; A61B 2017/0451; A61B 2017/0456; A61B 2017/0453; A61B 2017/0425

See application file for complete search history.

(56) References Cited

U.S. PATENT DOCUMENTS

| | | | | |
|---|---|---|---|---|
| 5,092,868 | A | * | 3/1992 | Mehdian ............ A61B 17/7053 606/74 |
| 5,540,703 | A | * | 7/1996 | Barker, Jr. ............... A61L 17/04 289/1.2 |
| 6,086,590 | A | | 7/2000 | Margulies et al. |
| 6,554,831 | B1 | | 4/2003 | Rivard et al. |
| 6,656,185 | B2 | * | 12/2003 | Gleason ................. A61B 17/82 24/135 R |

(Continued)

FOREIGN PATENT DOCUMENTS

| | | |
|---|---|---|
| FR | 2662073 A1 | 11/1991 |
| FR | 2890850 A1 | 3/2007 |
| WO | 2008146185 A1 | 12/2008 |

OTHER PUBLICATIONS

International Search Report of PCT/FR2012/000259 dated Aug. 9, 2012.

*Primary Examiner* — Pedro Philogene
*Assistant Examiner* — Lynnsy Summitt
(74) *Attorney, Agent, or Firm* — Banner & Witcoff, Ltd.

(57) ABSTRACT

The present invention relates to a vertebral fixation device (1) for holding a vertebra (V) on a rod (2), having a body (3) of U-shaped or substantially U-shaped cross section, a flexible band (4, 4') for connecting said vertebra to the fixation body which is provided with slits (17) for passage of the band and of means (M) for adjustably blocking the flexible band against the rod in the fixation body. The flexible hand (4, 4') comprises a loop (5, 5') closed on itself and provided with a flexible lamella (6, 6') which is able to form a guide for passage around the vertebra and into the fixation body.

11 Claims, 3 Drawing Sheets

(56) References Cited

U.S. PATENT DOCUMENTS 8,123,749 B2 * 2/2012 Serhan ............... A61B 17/0642
606/254

8,142,483 B2 * 3/2012 Drewry ............. A61B 17/7031
606/263
2009/0105715 A1 * 4/2009 Belliard ............ A61B 17/8869
606/103

* cited by examiner

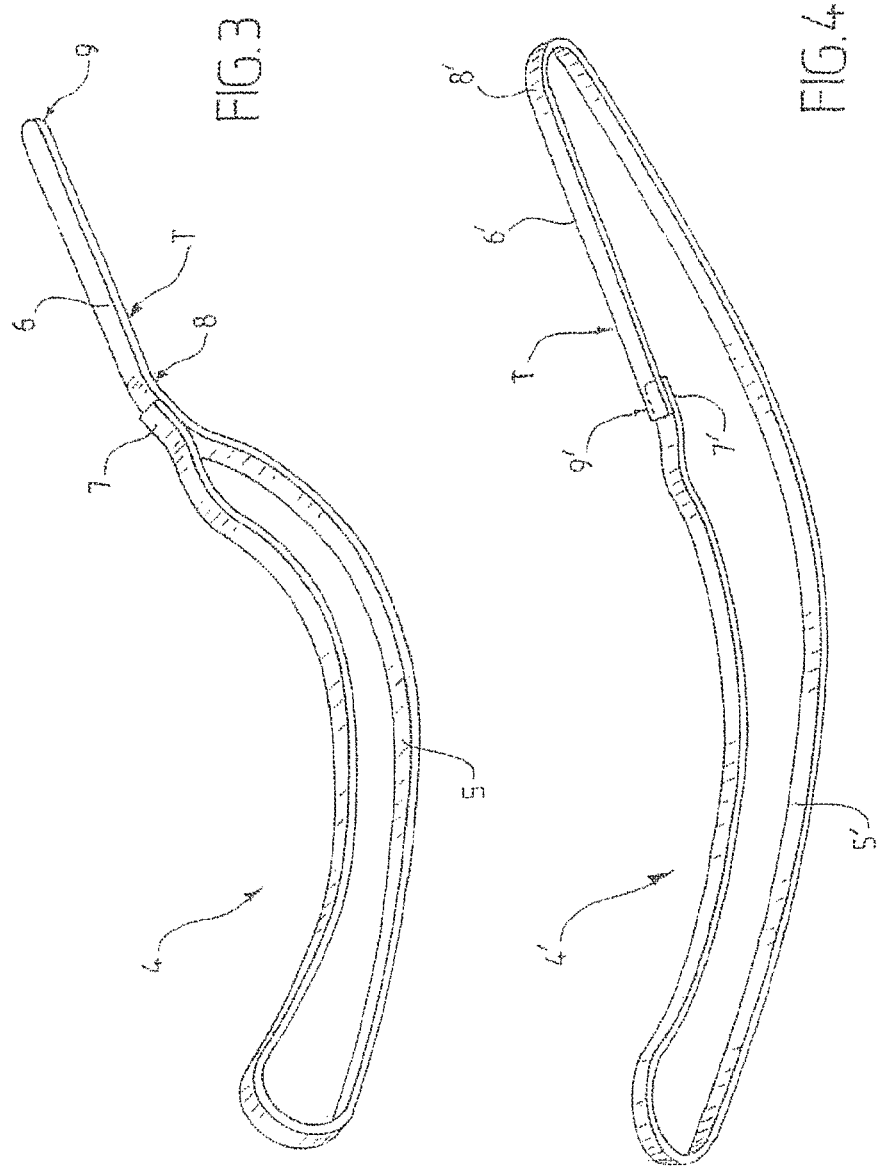

VERTEBRAL FIXATION DEVICE

The present invention relates to a vertebral fixation device for holding a spinal vertebra on a rod, comprising a body of U-shaped or substantially U-shaped cross section, a flexible band for connecting said vertebra to the fixation body, which is provided with slots for said band to mass through and means for adjustable immobilization of the flexible band against the rod in said fixation body.

It has a particularly important, although not exclusive, application in the field of straightening the vertebral column of a patient having an abnormal curvature.

In this case, the vertebrae not being aligned correctly with one another with respect to the vertebral axis, they have inclinations between them.

At certain positions, the side edges of the vertebrae will therefore lie closer together on one side and further away from one another on the other side.

In order to straighten the arrangement, it is known to reset the side edges of the vertebrae at a substantially equivalent distance on either side of the vertebral column, by means of rods connecting together either screws, which are inserted into the vertebrae themselves, or hooks, which are introduced along the spinal canal.

Such devices, however, have drawbacks.

Firstly, the use of screws is possible only if the vertebrae are in good condition and/or wide enough at the position of the fixation.

For its part, the use of hooks is very problematic because the operator must not touch the spinal cord for risk of paralyzing the patient.

In order to overcome these drawbacks, a system making it possible to avoid fixation screws or hooks has been proposed (FR 02 09 317 or FR 06 50 609).

The system comprises a flexible tie for fixing of the vertebra on a linking piece, which is itself fixed to the straightening rod.

Means for immobilizing the flexible tie by closure of the linking piece on the rod are provided. This system, however, again has drawbacks.

Specifically, articulation of the linking piece is necessary so as to permit lateral insertion of the rod and the flexible tie. The tie is moreover liable to slide over the vertebra and/or no longer grip it owing to the tensioning of other pieces linking to other vertebrae located in proximity and/or along the rod.

It is an object of the present invention to provide a vertebral fixation device which meets practical needs better than those previously known, particularly in that it will allow greater flexibility, better solidity owing to the absence of mechanical articulation which is always liable to blockage, and in that it has greatly improved adjustment possibilities and no risk of sliding and/or loss of tension on the vertebrae, and to do so at a lower cost.

It also has the advantage of straightforward handling of the band or flexible tie, allowing it to be inserted easily by the surgeon around the vertebra, which will for example allow effective fixation, in particular by means of a lark's head knot, which is impossible or very difficult to do with the device of the prior art.

To this end, the invention essentially provides a vertebral fixation device for holding a spinal vertebra on a rod, comprising said rod, a fixation body of U-shaped or substantially U-shaped cross section, a flexible band for connecting said vertebra to the fixation body, said fixation body comprising two slots for an band to pass through and means for adjustable immobilization of the flexible band against the rod in said fixation body, characterized, in that the flexible band forms a loop closed on itself and provided with a flexible lamella, said lamella being capable of forming a guide for passing around the vertebra and into the fixation body.

Advantageously, the flexible lamella is deformable, for example in order to adopt a hook shape allowing easier and more precise insertion.

In this way, the surgeon can modifiably shape it manually so as to pass better around the vertebra without risk of injuring the patient, the lamella being for example made of relatively soft flexible metal which keeps its shape by bending.

Thus, and with the invention, in particular by virtue of the great ease of introducing and/or positioning the band, excellent fixation on the vertebra is possible. The existence of the loop furthermore makes it possible to pass the lamella through it in order to immobilize the band on the vertebra.

Advantageously, in order to form the closed loop, the band has a first end fixed directly, for example by stitching or adhesive bonding, onto the other end or onto an end portion, which is itself terminated by said other or second end.

In other words, in order to form the loop, one end thereof is fixed immovably onto another part (end or intermediate point) of said band by adhesive bonding or stitching.

In advantageous embodiments, one or other of the following arrangements is employed:

The flexible band comprises a lark's head knot for fixation on the vertebra, the two strands coming from the knot passing over the same side of the rod into the fixation body, and being capable of being cut where they emerge, essentially level with the body, upstream of the flexible lamella;

the lamella is included in the loop;

the lamella is fixed outside the loop;

the means for adjustable immobilization are termed by a linking piece connecting the opposing ends of the two branches of the U, and the slots of the fixation body, for said band to pass through, are each formed respectively by an opposing recess located on the side of the bottom of the U, the immobilizing means being arranged in order to compress the rod against the wall and the opposing recesses being located, on the side of the bottom of the U for passage between said bottom and the rod;

the body is formed in a single piece;

the bottom of the U forming a bottom wall of the U, said wall is in the form of a half-cylinder with a shape complementary to that of the rod, terminated on either side by longitudinal edges allowing the rod to be clipped into the bottom of the U by virtue of deformation of the branches;

the linking piece is formed by a tightening screw provided on one side with a head for passing through a first branch of the U, said head comprising a frustoconical part arranged in order to compress the rod as it is being screwed, and on the other side with an end for screwing onto the opposite branch of the U;

the body of U-shaped cross section having a first branch of the U comprising an external face, the head of the tightening screw furthermore comprises a shoulder capable of interacting with the external face of the first branch of the U;

the fixation body is made of polymer material, the rod and the linking piece being made of titanium and the flexible band being a polymer braid.

The invention also relates to a method using a device as described above.

It also relates to a method for fixation of a spinal vertebra on a rod, with the aid of a device comprising a body of U-shaped or substantially U-shaped cross section, a flexible band for connecting said vertebra to the fixation body, which is provided with slots for said band to pass through, and means for adjustable immobilization of the flexible band against the rod in said fixation body, characterized in that, the flexible band comprising a loop closed on itself and provided with a flexible lamella at one end, one end of the loop folded on itself is passed around one branch of the vertebra on the opposite side from the lamella, in order to form a hoop outside the vertebra, and the flexible lamella is passed through the hoop in order to form a lark's head knot around said branch, which is tightened, said lamella is introduced into passage slots of the fixation body in the absence of the rod, the rod is introduced laterally into the body in order to compress the two strands of the loop against the bottom of the body, and is held with slight friction in the body, the body is slid into position in proximity to the vertebra, the flexible band is tensioned in order to bring the vertebra close to the rod, then the rod is compressed against the wall by the immobilizing means for final fixation, before cutting the strands of the loop extending beyond said body.

Advantageously, a tightening screw provided on one side with a passage head, said head comprising a frustoconical, part arranged in order to compress the rod as it is being screwed, and on the other side with an end for screwing onto the opposite branch of the U is screwed into a first branch of the U.

The invention will be understood more clearly on reading the following description of embodiments, which are given below by way of nonlimiting examples. The description refers to the accompanying drawings, in which:

FIGS. 3 and 4 are perspective views of a band according to two embodiments of the invention.

In the rest of the description, the same reference numbers will be used to denote the same elements.

Figure 1:
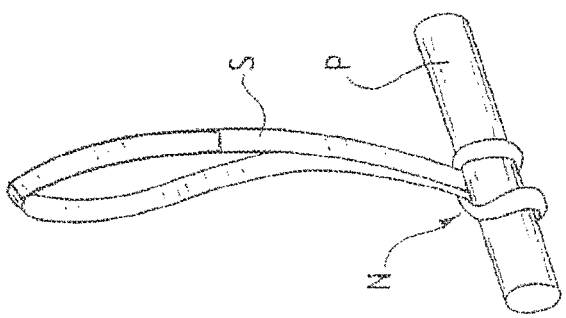
FIG. 1 is a perspective view of a principle of fixing the flexible band according to the invention.

FIG. 1 gives the principle of the lark's head knot N as produced with a band or strap S around a tubular niece P, which allows firm and immobilized fixation on one another.

Figure 2:
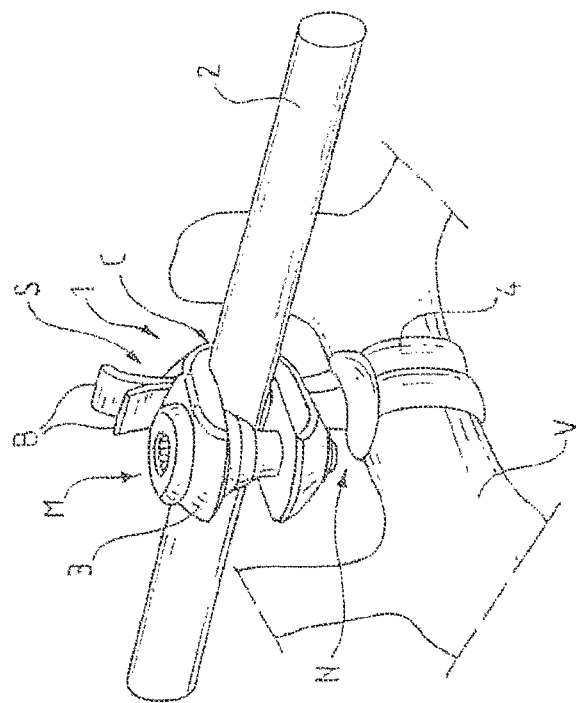
FIG. 2 shows an embodiment of the device on a vertebra, according to the invention.

FIG. 2 shows a vertebral fixation device for holding a spinal vertebra V (partially represented) on a cylindrical rod 2.

The device comprises a body 3 for fixation on the rod and a flexible band 4 of braided polymer, for example of polyester with a width of 6 mm and a length of thirty centimeters.

The flexible band 4 furthermore forms a lark's head knot N for fixation on the vertebra V, the two strands B of the knot passing over the same side C of the rod 2 into the fixation body 3, and being cut where they emerge S, essentially level with the body.

It also comprises means M for adjustable immobilization of the flexible band on the fixation body 3.

With reference to FIGS. 3 and 4, the flexible band 4, 4' comprises a closed loop 5, 5' provided with a flexible lamella 6, 6' either outside the loop (FIG. 3) or included in the loop (FIG. 4).

The lamella is for example made of very thin flexible steel with a thickness of from 0.1 mm to 0.5 mm, for example inserted into the braid T of the flexible band, the end 7, 7' of the band without lamella being connected to the lamella, for example being fixed by adhesive bonding or stitching on one side 8, referred to as the internal side, of the lamella (FIG. 3) or on the other side 9', referred to as the external side, of the lamella (FIG. 4).

In FIG. 2, it can be seen that the flexible hand a comprises a lark's head knot N for fixation on the vertebra.

Figure 5:
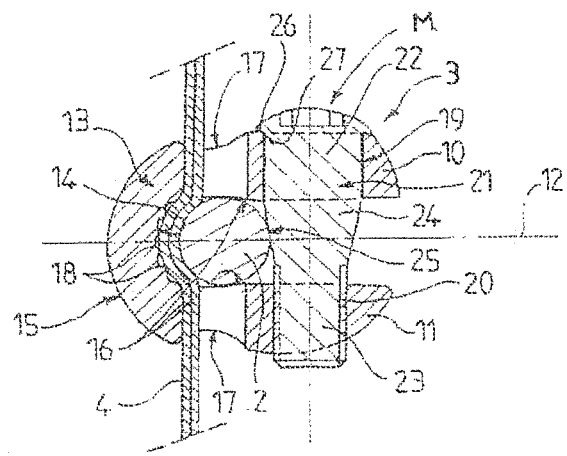
FIG. 5 is a sectional view of the body, the immobilizing means and a rod used with a device according to the embodiment of the invention more particularly described.

More precisely, with reference to FIG. 5, the body 3 is formed by a monobloc piece forming a clip having a U-shaped cross section, said U comprising two thick branches 10 and 11 of substantially half-oval-shaped cross section which are symmetrical with respect to a longitudinal plane 12 and are connected together by a linking part 13 in the shape of half a toric ring, forming on one side the semicylindrical bottom 14 of the U and on the other side a rounded external wall 15 of toric surface.

The bottom wall of the U has a shape complementary, or substantially complementary, to that of the rod 2, and comprises longitudinal lips or edges 16 allowing the rod to be clipped into the bottom of the U once the braid 4 has been passed through in double thickness (see also FIG. 2).

Each branch 10, 11 comprises a recess 17, for example in the form of a wide slot, for example 5 to 10 times wider than the thickness of the braid, in order to facilitate introduction thereof during the operation.

The bottom 14 of the U furthermore comprises notches 18 for non-return immobilization, which are parallel to the longitudinal plane 12 and have, in a manner known per se, ridges forming corners opposed or perpendicular to the sliding direction, opposing untightening of the loop once the tightening is exerted.

Each branch 10 and 11 comprises a respective cylindrical orifice 19 and 20 for the immobilizing means M to pass through, namely a bore 19 of diameter D and a threaded cylindrical screwing orifice 20 of diameter d<D.

The immobilizing means M are formed by a linking piece 21, or screw, provided on one side with a head 22 for passage into the bore 19 of the U, and on the other side with an end 23 for screwing into the threaded orifice 20.

The head 22 of the piece 21 comprises a cylindrical upper part which interacts in soft friction with the bore 19, said upper part being connected integrally to a frustoconical lower part 24, which tapers downward and is arranged in order to compress (bearing point 25 in FIG. 5) the rod 2 as the piece is screwed.

In the embodiment more particularly described here, the head of the screw furthermore comprises a shoulder 26, for example a frustoconical, shoulder, capable of interacting with the external face 27 of the first branch of the U and acting as an end-stop for the screwing.

Figure 6:
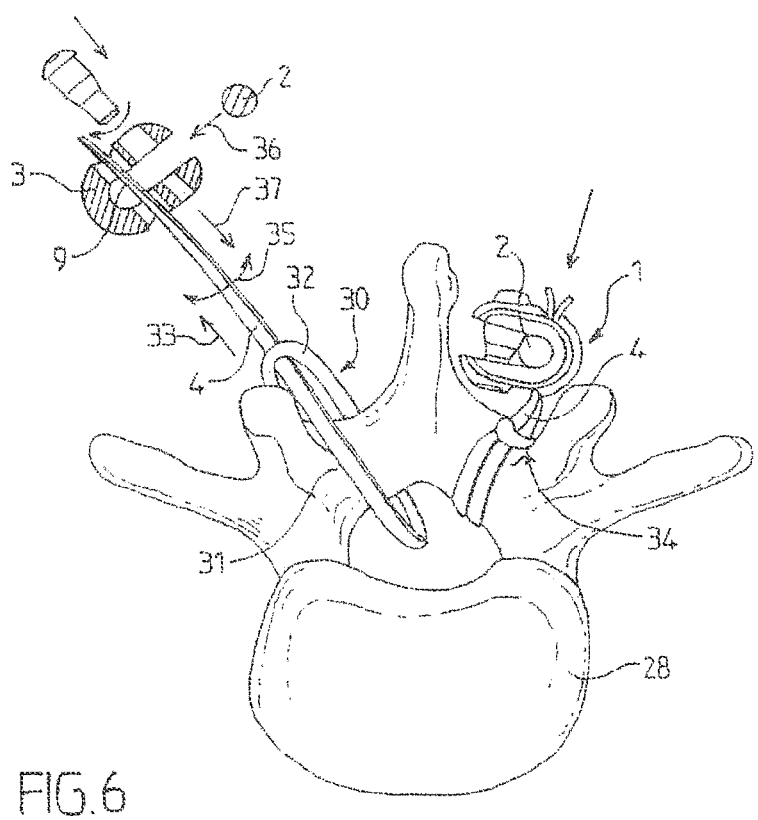
FIG. 6 shows, in a view from above, the device of FIG. 1 on one side in the course of being fixed, and on the other side fixed, on a vertebra.

The installation of the device 1 on the vertebra 28 will now be described with reference to FIG. 6.

The device 1 described above makes it possible to mechanically connect the flexible braid 4 onto the metal rod 2 for union with the vertebra 28.

This implant is particularly recommendable in the context of surgery on the spine of the type with scoliosis.

First (left-hand part of the figure) the end 30 of the loop folded on itself is passed around a branch. 31 of the vertebra 28, in order to form a hoop 32 outside the vertebra with respect to the branch 31 (here, the transverse lemma, posterior arch).

The lamella 9 is then passed through the hoop like a needle, through the loop, which is tightened (arrow 33) in order to form the lark's head knot 34 (see the right-hand part of the figure).

The braid 4 is then introduced into the body 3 through the slots 17.

After rotation (arrow 35) of the band, the rod 2 is then introduced (arrow 36) laterally into the body 3 in order to compress the two strands B of the loop against the bottom 14 with latching, which on the one hand leaves a possibility of sliding in view of the relative elasticity of the body, and on the other hand fixes the body on the rod and prevents it from falling.

The body is then slid, arrow 37, into position in proximity to the vertebra (see the right-hand part). The band is then tensioned by pulling on it through the body, with a suitable tool, and finally the rod is compressed onto the wall of the bottom by screwing.

The same operation is carried out on the adjacent vertebra or vertebrae which are intended to be repositioned with respect to one another, here in order to repair the scoliosis.

Only the fixation of a single body will be described below, the fixation of the others being carried out in the same way once their respective position along the rod is fixed.

The screw 22 is inserted into the bore 16, and then starts to be screwed into the bore 19.

The screwing is carried out by the surgeon, who has access to the screw heads, each provided with a screwing orifice and/or recess 28 known per se.

Once the assembly has been pre-positioned and while play remains on the braids, the latter are pulled so as to tighten the loops on the laminae of the respective vertebrae.

The non-return ridges 18 make it possible to tighten in one direction and prevent untightening in the other direction, when the two ends of the flexible band still remain slightly mobile.

The screwing of the screws 22 then allows the conical parts 24 to come progressively to bear on the union rod 2 until the assembly is locked, for each device immobilizing the braid 4 between the bottom of the U and the union rod by tightening.

As is evident, and as can likewise be seen from above, the present invention is not limited to the embodiments more particularly described. Rather, it encompasses all variants and particularly those in which two or more rods are fixed in line or on either side of the vertebral column.

The invention claimed is:

1. A vertebral fixation device for holding a spinal vertebra on a rod, comprising said rod, a fixation body of U-shaped or substantially U-shaped cross section, a flexible band for connecting said vertebra to the fixation body, said fixation body comprising two passage slots for said band to pass through and means for adjustable immobilization of the flexible band against the rod in said fixation body,
   wherein the flexible band forms a loop closed on itself and provided with a flexible lamella, said lamella being capable of forming a guide for passing around the vertebra and into the fixation body, and
   wherein the flexible band comprises a lark's head knot for fixation on the vertebra, said lark's head knot having two strands coming from the knot, said two strands passing over a same side of the rod into the fixation body via the passage slots.

2. The device as claimed in claim 1, wherein the lamella is included in the loop.

3. The device as claimed in claim 1, wherein the lamella is fixed outside the loop.

4. The device as claimed in claim 1, wherein the fixation body includes two branches presenting opposing ends, and a bottom, the means for adjustable immobilization are formed by a linking piece connecting said opposing ends of the two branches,
   wherein the passage slots of the fixation body, for said band to pass through, are each formed respectively by an opposing recess located on a side of the bottom of the fixation body, the means for adjustable immobilization being arranged in order to compress the rod against a wall of the bottom and the opposing recesses being located on the sides of the bottom of the body for passage of the flexible band between said bottom and the rod.

5. The device as claimed in claim 4, wherein the body is formed in a single piece.

6. The device as claimed in claim 5, wherein the bottom of the body forms said bottom wall, said bottom wall is in the form of a half-cylinder with a shape complementary to that of the rod, terminated on either side by longitudinal edges allowing the rod to be clipped into the bottom by virtue of deformation of the branches.

7. The device as claimed in claim 4, wherein the linking piece is formed by a tightening screw provided on one side with a head for passing through a first branch of the fixation body, said head comprising a frustoconical part arranged in order to compress the rod as it is being screwed, and on the other side with an end for screwing onto the opposite branch of the body.

8. The device as claimed in claim 7, wherein the first branch comprises an external face, and wherein the head of the tightening screw furthermore comprises a shoulder capable of interacting with said external face.

9. The device as claimed in claim 1, wherein the fixation body is made of polymer material, the rod and the linking piece being made of titanium and the flexible band being a polymer braid.

10. A method for fixation of a spinal vertebra on a rod, with the aid of a device comprising a fixation body of U-shaped or substantially U-shaped cross section, a flexible band for connecting said vertebra to the fixation body, said fixation body being provided with passage slots for said band to pass through and having a bottom, and means for adjustable immobilization of the flexible band against the rod in said fixation body,
   the flexible band comprising a loop closed on itself and provided with a flexible lamella at one end, wherein:
   one end of the loop folded on itself is passed around one branch of the vertebra on the opposite side from the lamella, in order to form a hoop outside the vertebra, and the flexible lamella is passed through the hoop in order to form a lark's head knot around said branch, which is tightened, said lark's head knot having two strands,
   said lamella is introduced into the passage slots of the fixation body in the absence of the rod,
   the rod is introduced laterally into the fixation body in order to compress the two strands of the lark's head knot against the bottom of the fixation body, said bottom having a wall, and is held with slight friction in the fixation body,
   the fixation body is slid into position in proximity to the vertebra,
   the flexible band is tensioned in order to bring the vertebra close to the rod,
   then the rod is compressed against the wall of the bottom by the means for adjustable immobilization, for final fixation, before cutting the strands of the lark's head knot extending beyond said body.

11. The method as claimed in claim 10, wherein said means for adjustable immobilization comprises a tightening screw provided on one side with a passage head, wherein the fixation body has two opposite branches, and wherein said head comprises a frustoconical part arranged in order to compress the rod as it is being screwed, and on the other side with an end for screwing onto a branch of the fixation body when it is screwed into the opposite branch of the fixation body.

* * * * *